United States Patent [19]

Yamamoto et al.

[11] Patent Number: 5,110,916

[45] Date of Patent: May 5, 1992

[54] BIS (OCTAALKYLPHTHALOCYANINATE) LANTHANIDES

[75] Inventors: Iwao Yamamoto, No. 16-25,2-chome, Fumiiri, Ueda City, Nagano Pref.; Kazuchika Ohta, Ueda; Tsuyoshi Komatsu, Okaya, all of Japan

[73] Assignees: Eastern Co., Ltd., Chino; Iwawo Yamamoto, Ueda, both of Japan; a part interest

[21] Appl. No.: 633,248

[22] Filed: Dec. 21, 1990

[30] Foreign Application Priority Data

Dec. 30, 1989 [JP] Japan .................. 1-340867

[51] Int. Cl.$^5$ .................................. C07F 5/00
[52] U.S. Cl. ........................................ 534/15; 540/139
[58] Field of Search ................................ 534/15; 540/139

[56] References Cited

U.S. PATENT DOCUMENTS 4,031,109 6/1977 Griffiths et al. .................. 540/139
4,784,736 11/1988 Lonsdale et al. .................. 540/139

OTHER PUBLICATIONS

Padilla et al., Inorg Chim Acta., vol. 172, (1990), pp. 241-245.

Konami et al. CA 113:13579x:; CA 112:90282b.
Kasuga et al. CA 94:39132k; CA 105:163838e.
Markovitsi et al. CA 107:66945w.
Collins et al. CA 103:94888r.
Moskalev et al. CA 85:153331p; CA 77:107325b; CA 67:28821a.
Moussavi et al. CA 142135v.
Tomilova et al. CA 64629t.

Primary Examiner—Robert L. Stoll
Assistant Examiner—C. Sayala
Attorney, Agent, or Firm—Dilworth & Barrese

[57] ABSTRACT

The present invention discloses lanthanide series bisphthalocyanine complex compounds, wherein chemically and thermally stable side chains effective for the development of a functional film due to generation of solubility and liquid crystallization in a solvent.

The compounds according to the present invention having no reacting positions at side chains thereof possess electrochromic properties and further possess excellent electrochemical characteristics. Moreover, these compounds are soluble in a solvent and show discotic liquid crystal phase. Therefore, these compounds are very effective for the development of a functional film.

21 Claims, 4 Drawing Sheets (a) metal free phthalocyanine absorption spectrum (b) lutetium complex absorption spectrum

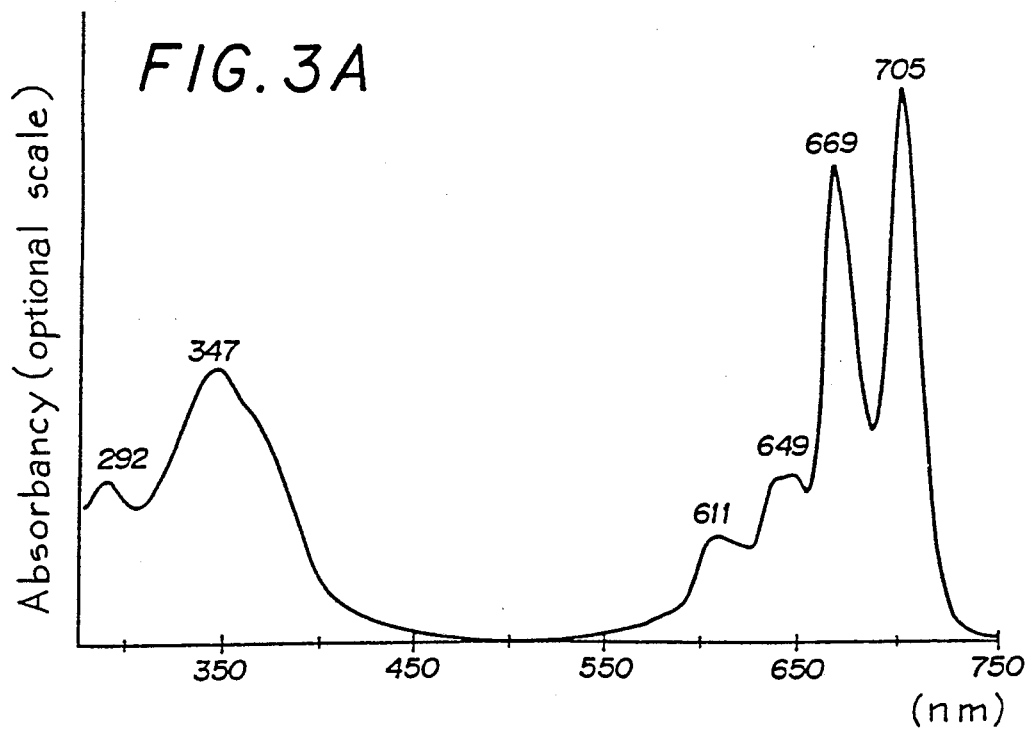
(a) metal free phthalocyanine absorption spectrum
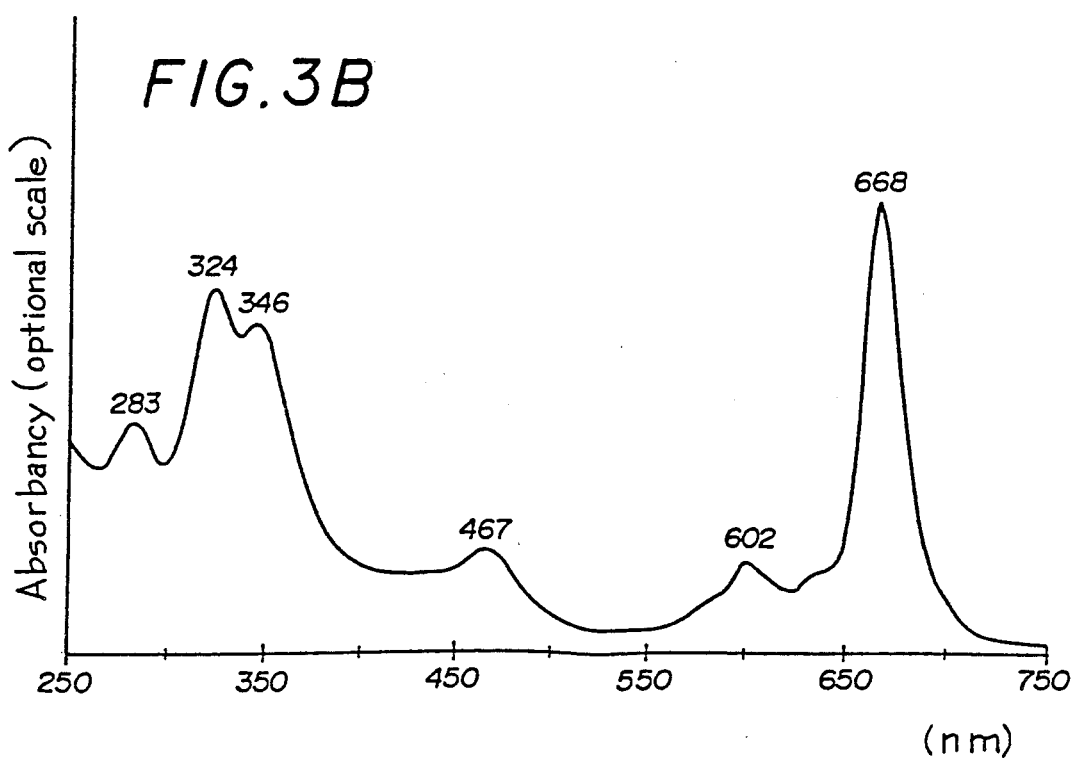
(b) lutetium complex absorption spectrum

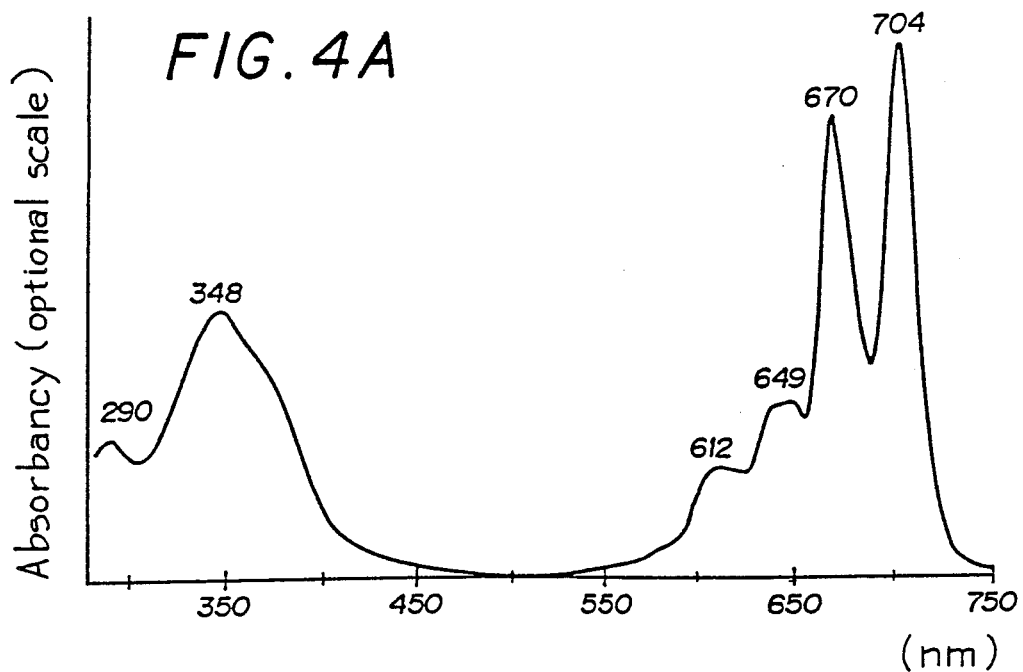
(a) metal free phthalocyanine absorption spectrum
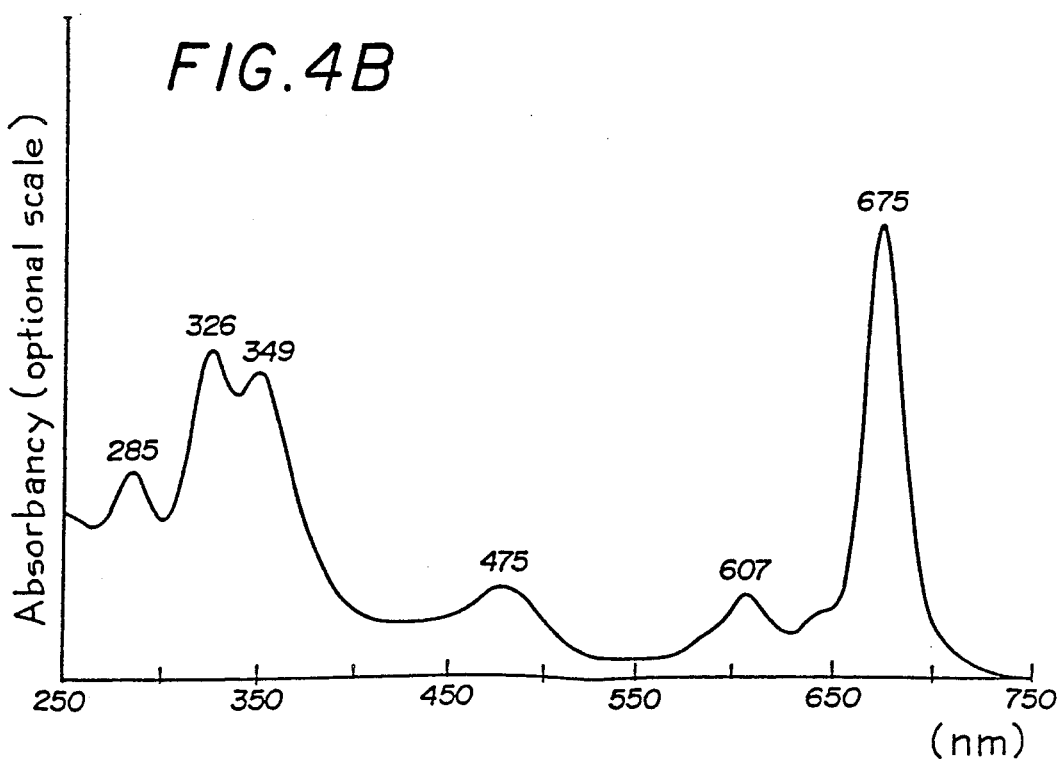
(b) lutetium complex absorption spectrum

BIS (OCTAALKYLPHTHALOCYANINATE) LANTHANIDES

BACKGROUND OF THE INVENTION

The present invention relates to lanthanide series-bisphthalocyanine complex compounds expected to generate excellent electrochemical characteristics such as electrochromism etc., wherein said compounds comprise chemically and thermally stable side chains effective for the development of functional film due to the generation of solubility and liquid crystallization in a solvent.

Hitherto, it has been expected that electrochromic substances may be put on display in practice under consideration that said compounds show discoloration by applying voltage thereto. Particularly, lutetium (or lanthanide series)-bisphthalocyanine complexes are being closely examined as one of few electrochromic substances having multi-color property. In general, phthalocyanine compound is insoluble in a solvent and the practicality thereof was limited, though it is easy to synthesize. Simon et al. have solved the aforementioned difficulty by applying eight long-chain alkoxyethyl groups to the circumference of phthalocyanine and further have proved that said substance exhibits liquid crystallization. Furthermore, the lanthanide series complexes not only exhibited an electrochromic property but also excellent electrochemical property such as an organic semi-conductor property. (For example, please see to French Patent "Brevet Francais" 84/19,348, FR 2,574,806). However, since the complexes have a hetero atom at the side chains thereof, said side chains become reactive and therefore stability as an electrochromic substance was a problem to be solved.

In order to solve the aforementioned problem, the present invention to mind provides electrical and thermal stabilities by introducing long chain alkyl group having no hetero atom as the side chains of lanthanide series bisphthalocyanine complexes. As a result of studies on phthalocyanine derivatives, the present invention has been achieved through various experiments by demonstrating that the lanthanide series complexes of octa (alkyl) phthalocyanine substituted at the 2, 3, 9, 10, 16, 17, 23 and 24 positions (shown by a general formula (1) below) with a long chain alkyl group have properties.

Hereinafter, an outline thereof will be described.

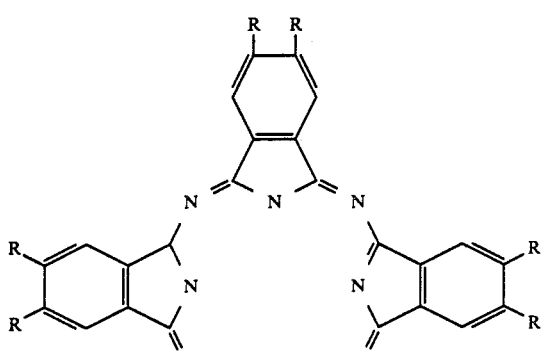

$(R_8P_c)_2L_n$

General formula (1)

(The right view is the construction).

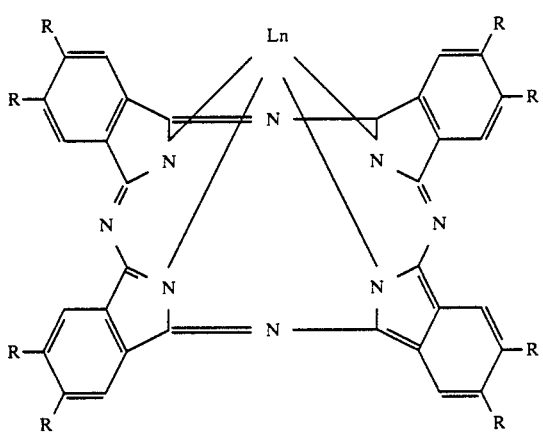

The general formula (1) is constituted in a manner such that two phthalocyanine rings are coordinated in a state of sandwiching the lanthanide series. In the formula, R is an alkyl group having 4-30 carbon atoms, and Ln is lanthanide series (La-Lu) and Yttrium. This empirical formula is written as $(R_8Pc)_2Ln$ where Pc represents phthalocyanine.

An exact structural formula (metal free) of octa-substituted phthalocyanine which is the ligand is shown as follows:

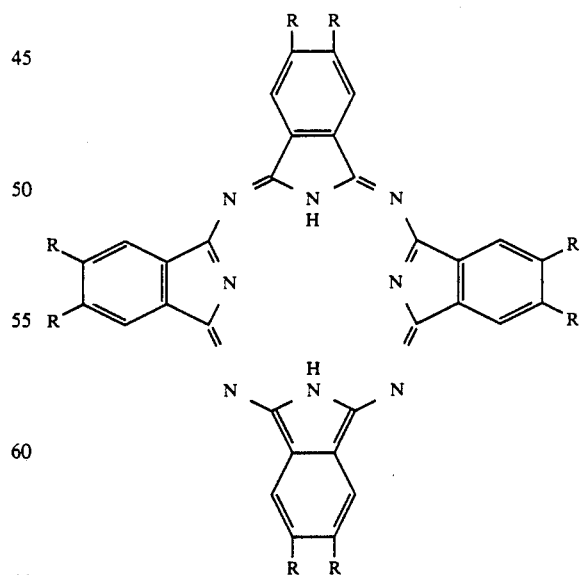

The above phthalocyanine is shown hereinafter as simply as possible;

wherein N atoms shown therein are N atoms of four pyrrole rings.

By employing the above simplified phthalocyanine model, the general formula (1) may be shown as follows: (Ln: Lanthanide series ions (La-Lu) and yttrium).

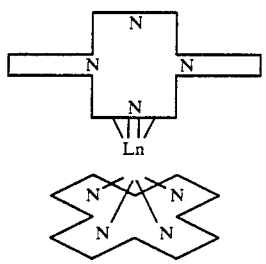

Free metal octasubstituted phthalocyanine was synthesized based upon the method of Simon and Ohta etc, New J. Chem., 12, 751 (1988). In detail, Grignard reagent prepared by alkylbromide and metal magnesium was reacted with orthodichlorobenzene and the dialkylbenzene 3 thus obtained was brominated so as to obtain dibromide 4 (FIG. 1).

Then, said dibromide 4 was reacted with copper (1) cyanide so as to obtain dicyanobenzene derivatives 5 (FIG. 1). Thereafter, metal free phthalocyanine was obtained under reaction in the presence of a base. Regarding the synthesis of phthalocyaninate) lutetium complex, a conventional well known method (e.g. Chem. Phys. Lett., 22, 124 (1985) by Simon et al.) was employed. In detail, phthalocyanine was treated with the base and thereafter was reacted with acetic lanthanide so as to obtain lanthanide series-bisphthalocyanine complexes shown in the general formula (1). R shown in the general formula (1) is an aliphatic alkyl group $C_4$-$C_{30}$ and R=$C_8$-$C_{18}$ is preferable in view of the treatment. (C: the number of carbon atoms). In the case where R=$C_{12}$, furthermore, the general formula (1) showed a monotropic and discotic liquid crystal phase. Further, the general formula (1) wherein R=$C_8$, $C_{12}$ and $C_{18}$ was generally of green color, but electrochromism showed red color at +0.29 V and blue color at −0.17 V.

BRIEF DESCRIPTION OF THE DRAWINGS

FIG. 3A is the absorption spectrum of metal free phthalocyanine of alkyl chain length 18;

FIG. 3B is the lutetium complex absorption spectrum thereof;

FIG. 4A is metal free phthalocyanine absorption spectrum of alkyl chain length 8; and FIG. 4B is the lutetium complex absorption spectrum thereof.

DESCRIPTION OF THE PREFERRED EMBODIMENTS

Embodiments of the present invention will be described in detail with reference to the drawings:

EXAMPLE 1

Method of preparing bis(octaalkylphthalocyaninate) lutetium (1.alkyl chain length 12)

In tetrahydrofuran (HF), Grignard reagent was prepared by 0.27 mol of n-lauric bromide and 0.27 mol of metal magnesium and then said reagent was reacted with 0.14 mol of orthodichlorobenzene in the presence of Ni catalyst. (yield 31%)

37.8 mol of bisdodecylbenzene thus produced and 41.6 mmol of bromine ($Br_2$) were reacted for 10 hours at 0° C.-5° C. in carbon tetrachloride so as to obtain monobromide. (yield 93%) Further, 32.1 mmol of the monobromide and 32.1 mmol of bromine were reacted for 21 hours at room temperature in dichloromethane so as to obtain dibromide. (yield 92%)

Figure 1:
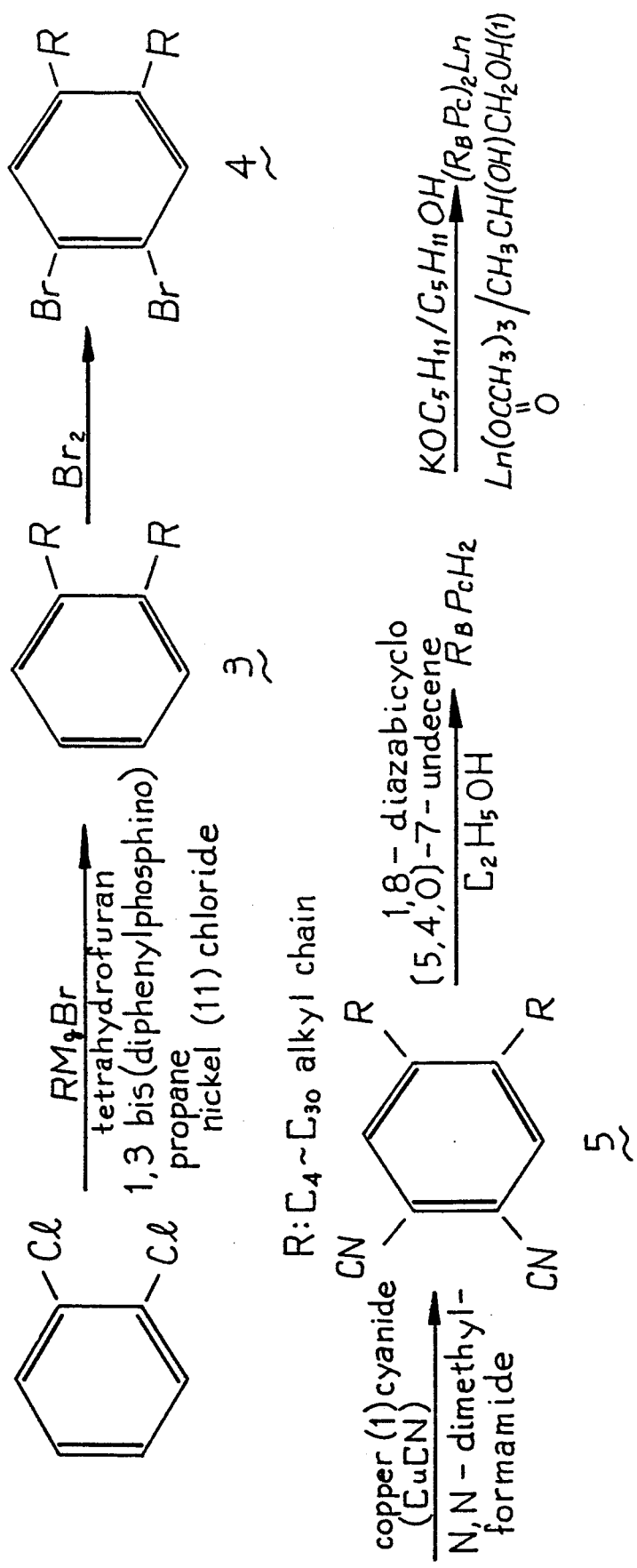
FIG. 1 is a flow chart of the synthesis of the compound according to the present invention.
Figure 2A:
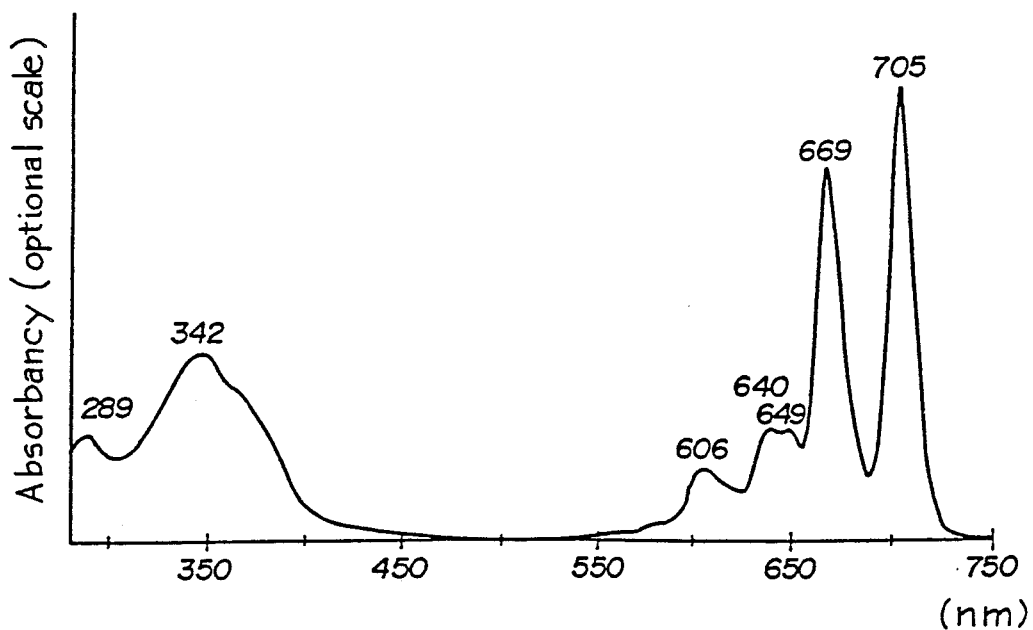
FIG. 2A is UV-VIS absorption spectrum of free metal phthalocyanine of alkyl chain length 12.
Figure 2B:
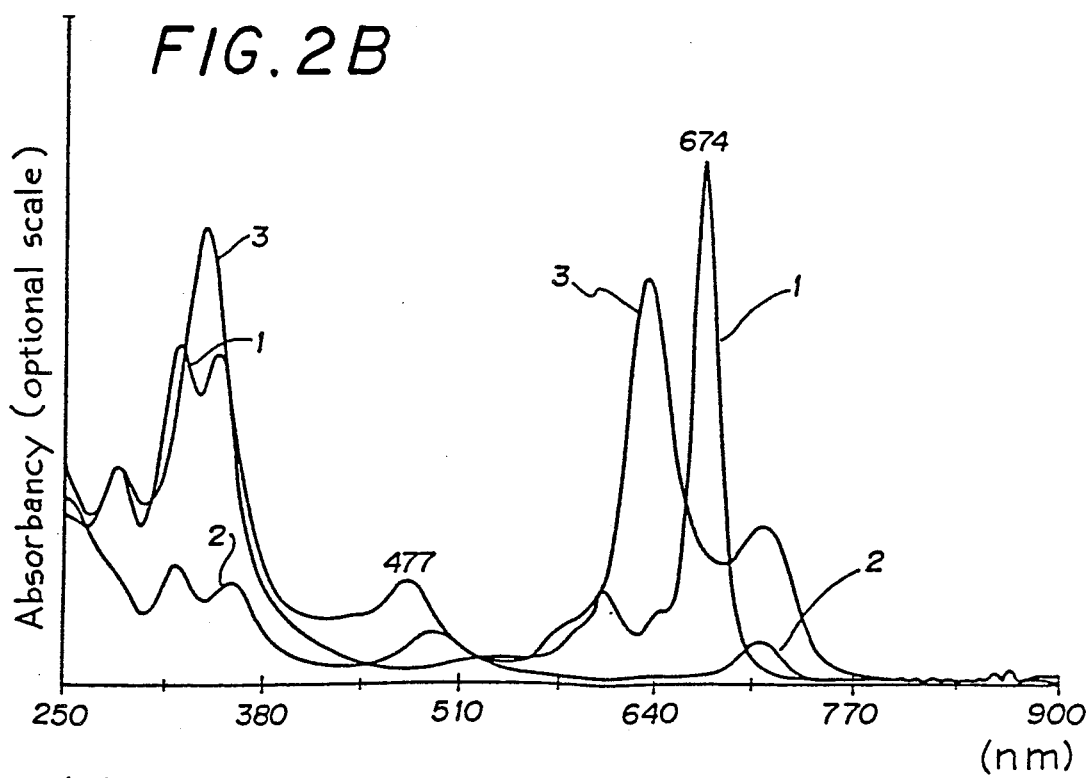
FIG. 2B is the absorption spectrum of the lutetium thereof.

17.5 mmol of dibromide and 55.0 mmol of copper (1) cyanide were subjected to reflux under heating for 6 hours in N,N-dimethylformamide (DMF) (yield 44%) and thereafter 0.43 mmol of dicyanobenzene derivative thus obtained was subjected to reflux under heating in ethanol in the presence of 1,8-diazabicyclo (5,4,0)-7-undecene (DBU) so as to obtain metal free phthalocyanine. (yield 25%) 107 $\mu$mol of phthalocyanine thus produced was treated with potassium amylate ($KOC_5H_{11}$) in amyl alcohol and further reacted with lutetium acetate so as to obtain the complex (1). (yield 28%) As a result of elementary analysis, hydrogen was 10.76% (calculated value: 10.77%). Carbon was 78.87% (calculated value: 78.9%) and nitrogen was 5.90% (calculated value: 5.76%). As result of ultraviolet-visible spectroscopy, as shown in FIG. 2B with line 1, characteristic absorption of lutetium was observed at 674 nm and 477 nm. Said absorption showed monotropic discotic liquid crystal phase at 32° C. to 44° C.

Table 1 shows a transition temperature.

TABLE 1

Transition temperature
($[(C_{12})_8P_c]_2L_n$ complex)

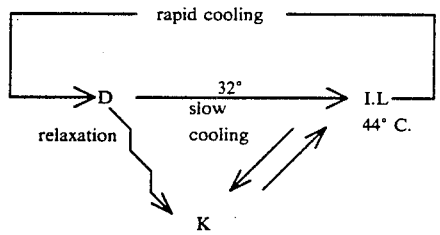

K: crystal phase
D: discotic liquid crystal phase
I.L.: isotropic liquid phase

Half wave electric potential by cyclic voltammetry was observed at −0.17 V and +0.28 V and discolorations from green to blue at −0.17 V and from green to red at +0.28 V were observed. Complex (1) is easily soluble and also refined except in a polar solvent. Ultraviolet visible spectroscopy of oxidant 2 and reductant 3 of (1) are shown in FIG. 2B.

EXAMPLE 2

Method of preparing bis(octaalkylphthalocyaninate) lutetium (1.alkyl chain length 18)

Grignard reagent was prepared by 0.11 mol of n-lauric stearyl and 0.11 mol of metal magnesium and said reagent was reacted with 0.05 mol of ortho-dichlorobenzene in the presence of Ni catalyst. (yield 39%) 17.2 mmol of benzene derivative thus produced and 34.4 mmol of bromine were reacted in dichloromethane so as to obtain dibromobenzene derivative. (yield 78%) 27.0 mmol of dibromide and 81.0 mmol of copper (1) cyanide were subjected to reflux under heating for 6 hours in DMF (yield 35%) and thereafter 55.0 mmol of dicyanobenzene derivative thus obtained was subjected to reflux under heating for 20 hours in ethanol in the presence of DBU so as to obtain metal free phthalocyanine (yield 13%), 95 μmol of phthalocyanine thus obtained was treated with potassium amylate in amyl alcohol and then reacted with acetate so as to obtain the complex. (yield 27%) As a result of elementary analysis, hydrogen was 11.50% (calculated value: 11.70%), carbon was 80.56% (calculated value: 80.69%) and nitrogen was 4.25% (calculated value: 4.28%).

As a result of ultraviolet visible spectroscopy, as shown in FIG. 3B, characteristic absorption of lutetium complex was observed at 668 nm and 467 nm.

Half wave electric potential by cyclic voltammetry was observed at −0.17 V and +0.29 V and discolorations from green to blue at −0.17 V and from green to red at +0.29 V were also observed. Ultraviolet visible spectroscopy of the oxidant and reductant showed the same spectrum as that of $R=C_{12}$.

EXAMPLE 3

Method of preparing bis(octaalkylphthalocyaninate) lutetium (1.alkyl chain length 8)

Grignard reagent was prepared by 0.26 mol of n-octyl-bromide and 0.26 mol of metal magnesium and said reagent was reacted with 0.13 mol of ortho-dichlorobenzene in the presence of Ni catalyst. (yield 36%) 39.6 mmol of benzene derivative thus produced and 79.4 m mol of bromine were reacted in dichloromethane so as to obtain dibromobenzene derivative. (yield 89%) 29.3 mmol of dibromide and 88.0 mmol of copper (1) cyanide were subjected to reflux under heating for 6 hours in DMF (yield 33%) and thereafter 7.1 mmol of dicyanobenzene derivative thus obtained were subjected to reflux under heating for 24 hours in ethanol in the presence of DBU so as to obtain metal free phthalocyanine. (yield 10%) 142 μmol of phthalocyanine thus obtained were treated with potassium amylate in amyl alcohol and further reacted with lutetium acetate so as to obtain the complex. (yield 23%). As a result of elementary analysis, hydrogen was 9.87% (calculated value: 9.69%), carbon was 76.37% (calculated value: 76.99%) and nitrogen was 7.51% (calculated value: 7.48%). As a result of ultraviolet visible spectroscopy, as shown in FIG. 4B, characteristic absorption of lutetium complex was observed at 675 nm and 475 nm.

Half wave electric potential by cyclic voltammetry was observed at −0.17 V and +0.28 V and discolorations from green to blue at −0.17 V and from green to red at +0.28 V were also observed. The ultraviolet visible spectroscopies showed the same spectrum as that of $R=C_{12}$.

The lanthanide series-bisphthalocyanine complex compounds having no reacting positions at the side chains obtainable according to the present invention exhibit electrochromism and further exhibit excellent electrochemical properties.

Furthermore, said lanthanide series-bisphthalocyanine complex compounds are soluble in a solvent and exhibit discotic liquid crystal phase and therefore there is a fair possibility of being a dielectric substance. Thus, said compounds are very effective for the development of a fundamental film due to a possibility of making a thin film.

What is claimed is:

1. A metal complex compound of the following formula:

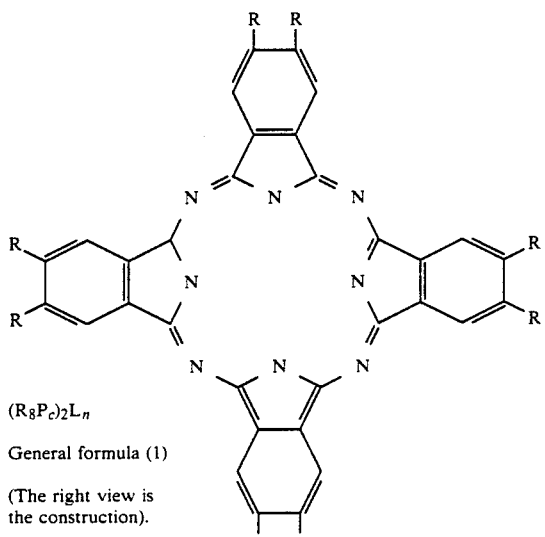

$(R_8P_c)_2L_n$

General formula (1)

(The right view is the construction).

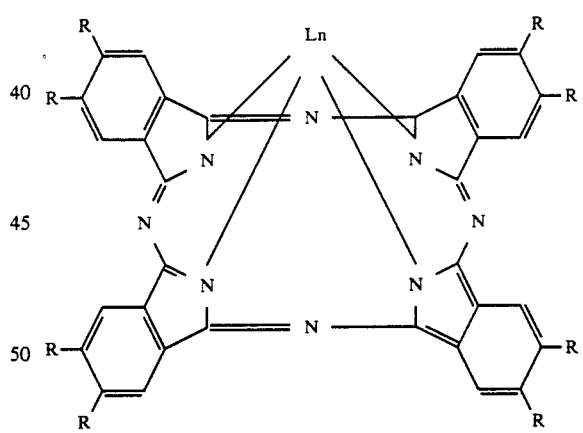

wherein R is an alkyl group of 4–30 carbon atoms and Ln represents one of the lanthanide series La–Lu or Y.

2. The compound of claim 1 wherein R is an alkyl group having 8 to 18 carbon atoms.

3. The compound of claim 2 wherein R is an alkyl group having 12 carbon atoms.

4. The compound of claim 1 wherein Ln is Lu.

5. The compound of claim 3 wherein Ln is Lu.

6. The compound of claim 2 wherein R is an alkyl group having 18 carbon atoms.

7. The compound of claim 6 wherein Ln is Lu.

8. The compound of claim 2 wherein R is an alkyl group having 8 carbon atoms.

9. The compound of claim 8 wherein Ln is Lu.

10. An electrochromic composition comprising at least one compound of the following formula:

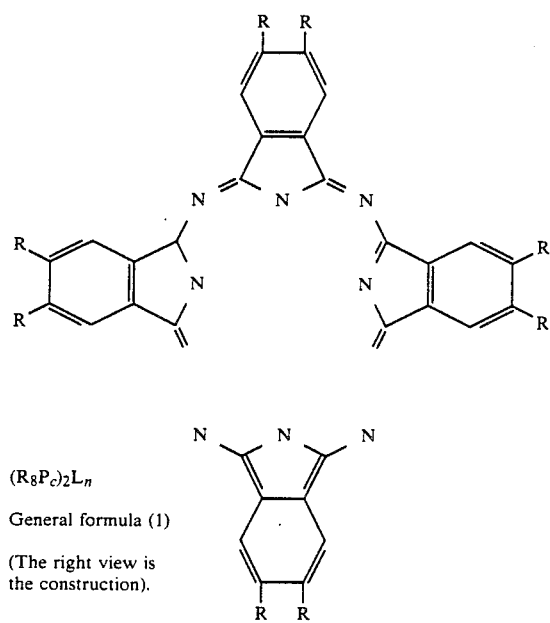

$(R_8P_c)_2L_n$

General formula (1)

(The right view is the construction).

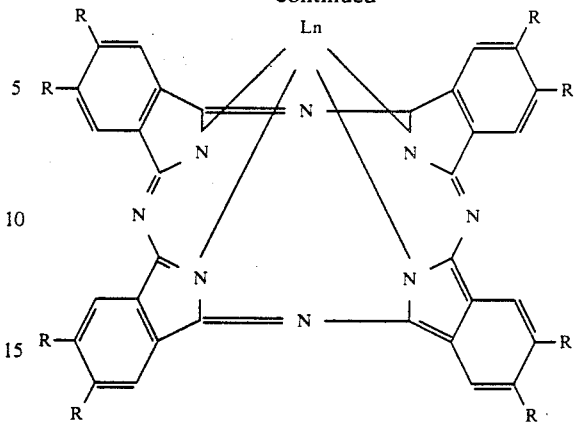

wherein R is alkyl group having 4–30 carbon atoms and $L_n$ is one of the lanthanide series La–Lu or Y.

11. The composition of claim 10 wherein R is an alkyl group having 8–18 carbon atoms.

12. The composition of claim 11 wherein R is an alkyl group having 12 carbon atoms.

13. The composition of claim 10 wherein Ln is Lu.

14. The composition of claim 12 wherein Ln is Lu.

15. The composition of claim 11 wherein R is an alkyl group having 18 carbon atoms.

16. The composition of claim 15 wherein Ln is Lu.

17. The composition of claim 11 wherein R is an alkyl group having 8 carbon atoms.

18. The composition of claim 17 wherein Ln is Lu.

19. The composition of claim 12 which is insoluble in a polar solvent.

20. The composition of claim 10 also exhibiting discotic liquid crystal phase characteristics.

21. The composition of claim 10 wherein the compound does not possess any reacting position along side chains R.

* * * * *